United States Patent
Jassan et al.

(10) Patent No.: US 11,358,120 B2
(45) Date of Patent: Jun. 14, 2022

(54) COMPOSITION OF MATTER FOR ADSORBING SCENTS AND RELEASING ACTIVE INGREDIENTS

(71) Applicants: Genaro Casas Jassan, Mexico City (MX); Jose Represas De Almeida, Mexico City (MX)

(72) Inventors: Genaro Casas Jassan, Mexico City (MX); Jose Represas De Almeida, Mexico City (MX)

(*) Notice: Subject to any disclaimer, the term of this patent is extended or adjusted under 35 U.S.C. 154(b) by 739 days.

(21) Appl. No.: 16/000,553

(22) Filed: Jun. 5, 2018

(65) Prior Publication Data

US 2019/0366299 A1 Dec. 5, 2019

(51) Int. Cl.
| | | |
|---|---|---|
| *B01J 20/24* | (2006.01) | |
| *B01J 20/16* | (2006.01) | |
| *B01J 20/10* | (2006.01) | |
| *B01J 20/32* | (2006.01) | |
| *A61L 9/013* | (2006.01) | |

(52) U.S. Cl.
CPC ............ *B01J 20/24* (2013.01); *A61L 9/013* (2013.01); *B01J 20/103* (2013.01); *B01J 20/165* (2013.01); *B01J 20/3244* (2013.01); *B01J 20/3274* (2013.01); *A61L 2209/22* (2013.01); *B01J 2220/46* (2013.01); *B01J 2220/485* (2013.01)

(58) Field of Classification Search
CPC ........ B01J 20/24; B01J 20/165; B01J 20/103; B01J 20/3244; B01J 20/3274; B01J 2220/485; B01J 2220/46; A61L 9/013; A61L 2209/22; A61L 9/042; A61L 9/04; C08L 97/005; C08L 97/02; C08L 99/00; A61K 8/9794; A61K 8/96; A61K 8/731; A61K 8/25; A61K 8/60; A61K 8/732; A61K 8/26; A61Q 15/00
See application file for complete search history.

(56) References Cited

U.S. PATENT DOCUMENTS

| | | | |
|---|---|---|---|
| 4,313,940 A | 2/1982 | Passarela | |
| 5,062,954 A * | 11/1991 | Leedy | C02F 1/681 210/502.1 |
| 5,064,407 A | 11/1991 | Peiffer | |
| 5,188,064 A * | 2/1993 | House | A01K 1/0154 119/172 |
| 5,207,389 A * | 5/1993 | Hall | A01N 25/12 241/21 |
| 5,891,937 A | 4/1999 | Berg et al. | |
| 6,053,125 A * | 4/2000 | Kory | A01K 1/0155 119/171 |
| 6,635,344 B1 | 10/2003 | de Almeida et al. | |
| 8,950,360 B2 * | 2/2015 | Wang | A01K 1/0154 119/171 |

* cited by examiner

*Primary Examiner* — Anthony J Zimmer
(74) *Attorney, Agent, or Firm* — Peter J. Rashid

(57) ABSTRACT

A composition of matter is described characterized by its qualities to adsorb scents present in gas, liquid and solid matter phases, while simultaneously serving as a carrier for an active ingredient or combination of active ingredients. The composition may also include an additive. The active ingredients are simultaneously and/or independently released gradually by the carrier, or a combination of carriers.

9 Claims, No Drawings

COMPOSITION OF MATTER FOR ADSORBING SCENTS AND RELEASING ACTIVE INGREDIENTS

FIELD OF THE INVENTION

A new product is described characterized by its quality as an adsorbent of undesirable scents present in the environment and at the same time by its quality as a carrier of fragrances, aromas and other active ingredients, which are simultaneously and/or independently released gradually by the carrier into the environment. The processes for obtaining the new product is also described.

BACKGROUND OF THE INVENTION

The search by mankind for absorption of unpleasant aromas and scents in the air that we breathe is as old as civilization. The earliest documents come from the Egyptians that used substances like charcoal, to adsorb from the air the scent of the cadavers in the mummification process.

Over the centuries these processes of purification for breathable air evolved in their technique, particularly at the beginning of the XX century due to the advent of toxic gases for military purposes. This evolution consisting in the filtration of breathable air has progressed to satisfy military and industrial necessities. Quick advances in the state of the art where made during the second half of the $20^{th}$ century, to improve the quality of the air in closed spaces, due to the contaminants in the air, generated by industry, transportation and in general by modern human activities. These filtration and purification systems in general are expensive and active in nature, requiring energy to circulate the air for its filtration.

On the other hand, the evolution of passive systems has been slow and not as effective as that of the active systems. Passive systems do not require energy to adsorb scents; fans or forced air through filters are not necessary to adsorb gases or undesirable substances in the air. Passive systems are characterized to be substances or products that exposed to the environment, adsorb, adsorb (accumulation on the surface) or react chemically to eliminate undesirable scents, gases or particles from the air.

The necessity to counteract or to eliminate, effectively and economically, the undesirable odors in the air has increased along with population growth, especially in urban concentrations since this is where the largest amount of pollutants and substances that bother human smell are generated. Examples of patents addressing this problem, are U.S. Pat. Nos. 5,944,704; 5,932,495; 5,932,147; 5,891,508; 5,861,147; 5,856,248; 5,807,364; 5,782,409; 5,733,272; 5,714,137 and the U.S. Pat. No. 5,593,670.

Examples common to the necessity of counteracting these polluting agents that cause bad odors are: the elimination of the aroma of tobacco smoke and its smell that impregnates closed spaces, such as houses, offices and automobiles. The malodor of garbage in kitchens, houses and buildings. The necessity to adsorb or to neutralize scents during storage of foods, ranging from domestic to commercial and industrial refrigerators. The previous examples are just a small sample of the dynamic and ever more complex universe of human beings and pets, cohabiting and using progressively more consumer goods in continuously reducing spaces.

In the combat of malodor scents, the most common and oldest is the one characterized by the use of substances that contain perfumes to mask scents. The masking of scents is the concealment of one smell by another, usually a malodor. However, the preferences for different aromas vary according to the individual and require relatively large amounts of perfume to counteract smelly malodor aromas.

Other forms of controlling malodor are, for example, the use of chemical substances. These processes are known in the state of the art as degradation by oxidation, where oxidizing agents such as: Chlorine bleach, Sodium hypochlorite, Chlorine Dioxide, and Potassium Permanganate are used. Other forms use degradation processes for reduction of malodor, these use active ingredients such as, Sodium Bisulfate to reduce malodor. These substances can be dangerous and aggressive for humans if used in direct form or exposed to the environment, they may also be harmful if in direct contact to cloths and many different surface materials.

Another method for the control of malodor is the use of active ingredients designed to react with smelly or malodor substances, by using specific chemical groups. Examples of these substances are the biguanid polymers that are mingled with organic compounds that contain atoms N and/or S, as well as the esters of fatty alcohols of Methyl Metacrylic that react with thiols, ammines and aldehydes. Their benefits are limited since they only react with certain very specific types of malodor.

Other types of well-known compounds are deodorants, in the state of the art these are antibacterial and fungicidal which destroy microorganisms that produce malodor. These compounds, typical in formulations of products for personal hygiene, are not effective in combating smelly substances that have already been generated and that do not come from sources like tobacco smoke or food.

Other forms of eliminating undesirable aromas from the air, are achieved, using adsorbent substances or products. Malodor particles or compounds stick to their molecular structure; these chemical compositions are the cause of malodor. Other adsorbent agents are characterized by admitting and retaining the malodor molecule inside their molecular structure. Among the more common adsorbent agents are charcoal, alkaline compounds such as sodium bicarbonate, aluminum silicates and Zeolite. Some chemical substances are also adsorbents, such as: Ciclodextrine whose intermolecular cavities admit small molecules of malodor. However, Ciclodextrin, especially when formulated in a watery solution, is considered fertile ground for microorganisms, given their important glucose content.

Finally, it is necessary to consider that conceptually there are two forms of achieving reduction or elimination of malodor. The first is called a passive system, meaning that upon exposure to the environment, the active ingredient or the adsorbent agent eliminates malodor scents from the surrounding air by contact. The second is an active system that achieves effectiveness by utilizing a mechanical devise. Most common are forced air systems that circulate air that in combination with adsorbent or active ingredients, filter, adsorb, perfume, or react chemically with malodor substances.

In U.S. Pat. No. 6,635,344, assigned to the assignee of the present invention, an adsorbent material of odoriferous substances from the environment comprises a carrier formed by particles obtained from one of a woody ring and a chaff ring of a corncob having a content of less than 1% of fines by weight and a moisture content below 10%. In one embodiment, an active ingredient is mixed with the carrier.

In U.S. Pat. No. 6,936,344, assigned to the assignee of the present invention, an adsorbent material of odoriferous substances from the environment comprises a carrier formed by particles consisting of a woody ring and a chaff ring of a corncob having a moisture content below 10%. In one embodiment, an active ingredient is mixed with the carrier.

In U.S. Pat. No. 7,163,737, assigned to the assignee of the present invention, an article of manufacture containing an adsorbent material of odoriferous substances, wherein the adsorbent material comprises a carrier formed by particles consisting of a woody ring and a chaff ring of a corncob having a moisture content below 10%. A method of manufacturing an article containing an adsorbent material of odoriferous substances comprises dispersing the adsorbent material within a fluff cellulose of the article.

In U.S. Pat. No. 7,247,377, assigned to the assignee of the present invention, an adsorbent composition of matter for controlled release of essential oils comprises a carrier consisting of particles obtained from woody ring and a chaff ring of a corncob, and an active ingredient mixed with the carrier, wherein the active ingredient comprises an essential oil. In another embodiment, the carrier consists of particles and an adherent substance, wherein the particle consists of one of a woody ring and a chaff ring of a corncob, and wherein the adherent substance is impregnated within the carrier; and an active ingredient mixed with the carrier, wherein the active ingredient comprises an essential oil.

In summary, U.S. Pat. Nos. 6,635,344, 6,936,344, 7,163,737 and 7,247,377 are directed to:

1. A carrier formed by particles obtained from one of the woody ring and chaff portion of the corncob;
2. The particles having less than 1% of fines by weight;
3. The particles having a moisture content below 10%;
4. An active ingredient mixed with the carrier consisting of polymers, fragrances, perfumes, flavors, oxidizers, attractants, repellents, reducers and antibacterials, in either a liquid or solid state; and
5. An adherent comprising a surfactant, mineral oil and an organic oil.

Although U.S. Pat. Nos. 6,635,344, 6,936,344, 7,163,737 and 7,247,377 worked well for adsorbing undesirable odors from the air, it is desirable to provide a carrier that is capable of adsorbing undesirable odors from all three states of matter: 1) gas; 2) liquid and 3) solid. In addition, it would be desirable to provide a carrier comprising a semi-rigid colloidal dispersion of a solid with a liquid or gas, such as a gel, jelly, glue, and the like, that is capable of adsorbing undesirable odors.

SUMMARY OF THE INVENTION

Embodiments of the invention are directed to a system for adsorbing undesirable odors and as a releaser of active substances. The system includes a composition of matter comprising a carrier obtained from all four (4) parts of a corncob (woody ring, chaff, bees wing or fine chaff, and pith), and/or other celluloses and/or their basic chemical compositions, such as, but not limited to, saw dust, granules or particles from any type of wood, powder, shavings, granules or particles from bamboo powder or flour, milled straw, cellulose, hemicelluloses, lignin, adsorbent minerals, such as, but not limited to, silica and zeolite, polysaccharides, such as dextrose and starch, either individually or mixed.

The system may also include an active ingredient that is mixed with the carrier. The active ingredient may comprise polymers, fragrances, perfumes, flavors, oxidizers, attractants, repellents, reducers, anti-bacterial, fertilizers, pesticides, hormones and enzymes in a gas, liquid or a solid, or any combination of the above, and semi-rigid colloidal dispersions of a solid with a liquid or gas, such as a gel, jelly, glue, and the like.

The system may also include an additive comprising a mineral oil, an organic oil, a colorant, a surfactant, a solvent, a lignin additive, a pH buffer, and any combination thereof.

The functional objective of this invention, is that this composition of matter gathers three simultaneous qualities: 1) adsorbs undesirable scents present in gas, liquid and solid matter phases; 2) simultaneously releases different types of active ingredients, into gas, liquid or solid surroundings; and 3) operates efficiently and economically by being a passive agent that does not require use of energy and its associated operating cost.

Additionally, it is necessary to contemplate other factors that are concurrent in the present invention and that are part of the new product, object of this invention in its functional aspects:

First, current tendencies prefer the use of organic and biodegradable materials, such is the case of this adsorbent carrier that while adsorbing malodors and releasing active ingredients into its surrounding, is compatible with the environment and easily disposable and recyclable in nature.

Second, covered under the concept of aromas we find pleasant smelling substances perceivable to the human sense of smell, as well as other substances that without being significantly disagreeable to humans may be used as repellents or attractants for other species. The composition of matter object of this invention can also be used as a carrier for repellents or attractants to species like insects, microorganisms, reptiles, mammals, and the like.

The concept of the new product derived from the present invention, is enlarged in its range of applications. For example, uses in agriculture, home and industry are possible by combining its qualities to adsorb undesirable odor and gradually release an active substance to repel, control or kill plagues of insects, like cockroaches in kitchens or mosquitoes as well as other agricultural crop damaging insects. Good results are obtained by combining a substance like Nepetalactone, known for its qualities as a repellent of cockroaches or garlic known for its qualities as a repellent for garden or agriculture damaging insects, with this adsorbent carrier. Additionally, the adsorbent carrier has the capacity to gradually release these forms of active ingredients providing for a long-lasting product; malodor, if present is also adsorbed. Inversely, attractant substances can be used, being of particularly useful application for household pets, for example, the use of an attractant aroma or fragrance in the production of cat litter.

Third, the adsorbent agent can be combined with other chemical substances whose properties allow them to react chemically with aromas present in the air. This includes the use of substances not perceived by human smell. Such as oxidizing agents or reducers that can help neutralize the concurrence of diverse aromas, like those present in a refrigerator. Simultaneously, the aroma absorption capacity of the carrier comes into effect resulting in a refrigerator that doesn't smell.

Another example for the use of the composition of matter subject of this invention, is its use for medicinal and therapeutic use. As is the case of aromatherapy, where the carrier releases into the air of a room, automobile, or office, aromas of medicinal type in accordance to the results a user is trying to achieve, for example: aroma of thyme, *eucalyptus* or other to alleviate breathing congestion.

Fourth, the product of the present invention fulfills the qualities of adsorption of malodor and/or the release of aromas or fragrances in a passive way, when being exposed to the environment in any container that allows it's contact with the air around it. The new product can also be used as a substantial component in active systems, since it can be adapted to all type of air conditioning, heating, air filtration, air care, industrial or commercial spaces as well as transportation vehicles. Functionality is mostly dependent on the use of an appropriate container that adapts to the required air intake of the system in question.

The qualities of the new product are more obvious and more effective in active systems of air filtration and conditioning, characterized by recycling air in relatively reduced spaces, such as automobiles, airplanes and public transportation vehicles. The intensity and duration of the aroma or fragrance released in the air through active systems, can be controlled by the concentration of aromas, fragrances or active substances to be used as well as it's adequate formulation, according to the knowledge available for the state of the art.

The effectiveness and duration of this new product in combination with active systems, will depend on the adsorbent agent's volume and this amount is calculated in direct relationship to the volume and air speed that the active system moves in a given period of time.

In one aspect of the invention, a system for adsorption of undesirable odors comprises a carrier; an active ingredient mixed with the carrier; and an additive.

In another aspect of the invention, a composition of matter for adsorption of undesirable odors comprises a carrier; and an active ingredient mixed with the carrier.

DETAILED DESCRIPTION OF THE INVENTION

In the following specification and the claims, a number of terms are referenced that have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the terms "adsorb" or "adsorbent" are synonymous with chemical adsorption, chemisorptions, physical adsorption or physisorption.

As used herein, "malodor" is defined as a very unpleasant smell.

As used herein "scent" is defined as a distinctive, often agreeable odor. The invention adsorbs or absorbs both pleasant (i.e., "scents") and unpleasant (i.e., "malodors") odors.

Structurally, the corncob is composed of four constituent portions, namely the beeswing, the chaff, the woody ring and the pith. In comparison, the beeswing, chaff and pith portions of the corncob are much lighter weight and much more adsorbent than is the woody ring portion of the corncob. A typical quantitative analysis is as follows:

| Item | Weight, Grams | Proportion of corncob, Percent |
|---|---|---|
| Corncob, whole | 46.3 | 100.0 |
| Corncob, fractions: | | |
| Woody ring | 27.9 | 60.3 |
| Chaff and beeswing | 17.5 | 37.8 |
| Pith | 0.9 | 1.9 |

In one embodiment, the composition of matter of the present invention consists of two basic elements: first, a carrier characterized by its great capacity for odor and malodor absorption, and gradual release of other active substances toward the air or to its surroundings. Second, one or more chemical, natural or synthetic elements that added to the carrier complete diverse functions, according to the desired results (perfume surrounding air, react with undesirable substances present in the air, liberate therapeutic, repellent, biocide or attractant chemical agents).

The carrier which is the preferred embodiment of the product in the present invention is a material obtained from the threshed ear of corn (Zea maiz) whose special physical and chemical qualities al low the previously described functions, of absorption and gradual release. To obtain the different components that comprise the threshed ear of corn, an industrial process, well known in the state of the art is required, which consists of separation, classification and sizing of each one of the components that constitute corncobs.

The threshed ear of the corn, also known as "olote" in Mexico, "spiga de maiz" in Castilian, corncob in English, "sabugo" in Portuguese and "balle de mats" in French, if cut transversely is constituted by three concentric ring. Starting with the inner ring, they are known in English as pith, woody ring and chaff. The material of the present invention uses the woody ring, chaff, bees wing or fine chaff and pith portions.

The woody ring, as well as the chaff portions have similar characteristics, both can be used as carriers for active ingredients as described in the body of the present invention. The main differences reside in the difference of absorption capacity and in the particle hardness. Other differences exist and are described below.

In order for the woody ring to comply with the requirements of the present invention it must have the following characteristics: woody ring should be about 99% free of other cob particles, it should have no more than about 1% dust or fines (the product should be air washed). It must be subjected to heat treatment that guarantees microbiology content and moisture levels under about 13%. For correct functionality, the particle size should be uniform in size and ranges should not exceed a maximum of about 2380 microns and a minimum of about 250 microns.

The woody ring of corncobs is characterized by the following: a hardness of about 4.5 on the Mohs scale, a fast absorbency of oil (for example soybean oil) of one-to-one on weight basis and the typical molecular structure of a natural fiber. Ideally particle sizing for the present invention should be between the following ranges: 1) retained or larger than a mesh of about 2380 microns, 2) particles between about 2380 and about 1191 microns, 3) particles between about 1191 and about 841 microns, 4) particles between about 841 and about 420 microns.

The main characteristic of the particle size is the contact surface that each one represents; for example, particles between about 1410 and about 841 microns have an average contact surface of about 5.88 square meters per gram. Particles between about 841 and about 420 microns have an average contact surface of about 7.20 square meters per gram. This characteristic is decisive in the qualities of absorption of different substances on the part of the carrier that embodies the product object of the present invention.

It is necessary to highlight that woody ring particles are characterized by having a structure that seen on an electron microscope, resembles that of a sea sponge. One can infer that this type structure has capacity to admit and retain substances of small and large molecular size. This allows superior qualities of absorption in comparison to other products such as Ciclodextrines that as is known in the state of the art, only admits malodor molecules of small size.

The separate and classified sizes of woody ring have unique qualities for the absorption of scents from the air in contact with them. To illustrate this, diverse laboratory tests were made with surprising results as follows:

Example #1

A 100 gram portion of mature Camembert cheese, a 20 gram portion of bacon and a 10 cm dish containing about 25 grams of woody ring particles sized between about 1410 and about 841 microns where all placed in a sealed glass container. Another glass container with the same components except for the woody ring particles was also prepared as a control sample. Both glass containers were inspected at intervals of 24 hours, 3 days, 5 days and 8 days; the container with the adsorbent material practically didn't manifest the characteristic scent of the decomposition of products contained, while the control glass container presented potent and unpleasant scents.

Example #2

10 grams of tobacco where incinerated in two sealed glass containers. One of the containers had a 10 cm diameter dish containing 10 grams of woody ring, sized between about 1410 and about 841 microns. The other container remained as a control sample. After 24 hours both containers where opened. The container with the adsorbent woody ring particles did not present the characteristic scent of tobacco, while the control sample presented potent scents characteristic of tobacco smoke.

In both examples, the evaluation of the scents or aromas were carried out by the authors of the present invention, as well as by a professional perfumist whose educated sense of the smell surrendered an objective opinion of these examples.

The characteristics of the Chaff portion of the corncob are similar to the woody ring portion in its ability to function as a carrier for fragrances and other active ingredients. The most distinguishing differences are: 1) more absorption; between 1.5 and 3 times it's weight in oil. 2) Particles size between about 841 and about 73 microns and 3) less particle flowability. Woody ring particles are rounder in shape than chaff and therefore flow better.

This physical difference between woody ring particles and chaff particles is translated into functional differences in the ability to adsorb undesirable scents from the air. Additionally, the granular form of the woody ring allows for more interparticle space for airflow. While the smaller closer chaff particles allow less airflow.

Both woody ring and chaff are characterized by having an almost neutral pH, in the order of about 6. This quality makes it an ideal inert carrier with all type of substances, since it does not react with active ingredients. Some other types of carriers have to be deactivated first to neutralize their pH content.

The physical and chemical characteristics of corncobs are not favorable for the development of microorganisms, therefore not providing fertile ground for bacteria or fungi that in turn cause malodor or disagreeable scents. It is known in the state of the art that a whole corncob can be stored without cover for periods of one year.

The functional differences of the woody ring portion (flowability and larger interparticle space) and that of the chaff (more absorption) allow for a great diversity of applications and use. These corncob fractions can be used combined or separately, for different applications, that are described for the adsorbent carrier that integrates the product object of the present invention.

For example, if the functional objective, is the absorption of an active substance to be slowly released in the air and at the same time allowing the flow of malodor air to be adsorbed, the suitable product is the one obtained from the woody ring. If on the contrary the functional object is to achieve absorption of an active substance to be slowly released in the air and the absorption of malodors or scents is not important, the elected product would be the chaff portion.

Other approaches to select the corncob fraction can be: the convenience of not having powders or fines. An example of such an application is the integration of the adsorbent agent to active filtration systems where the use of the product from the woody ring is most suitable. If the active ingredient required is thick in nature or if product were required to be molded in a three-dimensional object (including the making of pellets), one would be inclined to select the chaff portion.

On the other hand, and a substantial element of the composition of matter, object of the present invention, are the active substances or ingredients to be used. These can be aromas, perfumes, flavors or other natural or chemical agents that are integrated to the product derived from the composition of matter object of the present invention. In general, these substances are available in a liquid, powder or granular state and depending on the active agents chemical constitution, soluble in oil or water.

Under these conditions the adsorbent carrier, depending on the type of active ingredients used, can adsorb a larger or smaller quantity of said agent. This depends primarily on the size of the active ingredient molecule size, the adsorbent carriers gradual release will also depend on this molecular size. The absorption of malodor or scents is simultaneously achieved. The intensity, duration and brightness of the aroma, with fragrances, will depend on factors of the active ingredient or agent's composition. For example, larger molecular size is equal to longer duration, while the presence of smaller molecular sizes such as those in an ester, evaporate quickly.

Some examples for the formulation of the adsorbent carrier with active substances in a liquid state are:

Example #1

For fragrances, perfumes and therapeutic aromas, generally using a base of polyvinyl glycol, light mineral oil or microencapsulated powder or granular base, the concentration on a weight basis of the woody ring to active ingredient, is from about 0.01% to about 18%. A larger amount saturates the adsorbent carrier and product flowability is greatly reduced. For concentrations on a weight basis of the chaff portion ranges from about 0.01% to about 36% are required.

Example #2

For repellents and attractants, generally in oleaginous or microencapsulated powder or granular bases such as Givaudans Flavor Burst™ products, the recommended concentration ranges, for the woody ring as well as the chaff portion, are similar to the previous example. Concentrations depend on the active ingredient or agent used and the functionality desired in the end product.

Example #3

For oxidizers and chemical reducers or neutralizers, generally in a liquid or solid microencapsulated powder or granular base, the concentration ranges on a per weight basis, both for woody ring and chaff are from about 0.05% to about 5% of active ingredient or substance. Being that the determinant factor is not the capacity of carrier absorption, but rather the capacity to stay stable and not be affected by the active substance.

Example #4

For antibacterial and fungicidal use, when these are in a water, oleaginous or microencapsulated powder or granular base, the proportion of active ingredient or agent on a per weight basis to adsorbent carrier is the same as that of example #1. When the active ingredient uses a water base, the concentrations on a per weight basis can range from about 0.01% to about 25% with the woody ring fraction and about 0.01% to about 50% with chaff. The concentration to choose will be determined by the experience of whom ever prepares formulations according to the known state of the art.

Additionally, as mentioned in previous examples, the formulation of the composition of matter or product object of the invention, can be made using liquid based active ingredients added to the adsorbent carrier. The possibility also exists for the use of solid materials as active ingredients, usually in the form of pure or microencapsulated products. This variation allows more flexibility in the adsorbent carriers' applications. It can also take advantage of factors like stronger concentrations of active ingredients. Many pure substances come in solid form; the use of a liquid as diluent or dispersant of the pure substance implies a reduction in its concentration or strength. For example, table salt NaCl is more intense to the palate than its version diluted in water, commonly called brine.

On the other hand, the use of active ingredients in solid state can adhere and/or adsorb to the surface of the adsorbent corn cob carrier, allowing it to use a larger proportion of its inner adsorbent capacity for malodor or other applications. The opposite occurs when using active ingredients in a liquid state, since these occupy more of the corncob carriers' odor adsorbent capacity thus partially reducing its ability to adsorb undesirable malodor.

The option of using active ingredients in solid state instead of liquid, is possible with the concurrence of 4 basic elements: an adsorbent carrier, constituted by a fraction derived from corncobs, an active ingredient or agent that is in liquid or solid state; a combination resulting from the mix of a mineral or organic carrier with a liquid base active ingredient and finally, a substance that assures that, the active ingredients adsorb or absorb to the corncob carrier (avoiding the separation among carriers or agents and assuring correct homogeneity, functionality and dispersion).

To exemplify the above-mentioned, we describe two practical examples. The results obtained, using two types of active ingredients one in liquid form and the other solid, both dispersed in the corncob carrier; woody ring sized between about 1410 and about 841 microns was used. The liquid active ingredient is a concentrated floral fragrance perfume using polyvinyl glycol as a carrier.

Example #5

Corncob carrier mixed with an active ingredient in is a liquid base.

The density of the active ingredient determined a saturation point of about 18% on a per weight basis to the corncob granules. 180 grams of active ingredient where mixed with a kilogram of corncob carrier. This proportion maintains carrier flowability, absorption of odors and slow release of active ingredient (fragrance).

Results: the perfuming active ingredient, was released gradually and perceived smell lasted 30 days. The corncob carrier continued adsorbing scents in the air after 30 days.

Example #6

Two active ingredients; one utilizing an encapsulated active ingredient, commercially available, like Givaudan fragrance or flavor, in powder form and the other, using a laboratory sample, made by mixing Silicon Dioxide (SiO2), in proportion of 1 to 4 on the base of liquid active ingredient to Silicon Dioxide weight. The adsorbent corncob carrier was impregnated with an adherent coating, in this case consisting of about 0.5% per weight basis, foamed solution of anionic surfactant with water. Once the corncob carrier was mixed with the foam, an adherent coating of foam formed on the corncob granules. Immediately after which the active ingredients in solid form where added. The active ingredient particles adhered to the coating and allowed for a homogeneous mixture without separation.

Results: In both cases the adhesion of solid particles to the corncob granules allowed a more intense and prolonged duration of the perfuming scent, which was slowly released over a 60 day period, in comparison to the 30 days obtained in example #5 with a liquid active ingredient perfume mixed directly with corncob granules. In both cases the corncob adsorbed odors in the air even after 60 days.

Both examples, one with liquid and the other with solid active ingredients were performed at the same time. The new product was exposed to the air by placing it in a 40 cm×5 cm dish. The product was placed in two separate rooms measuring 3×4×2.4 mts.

The adherents used to form a coating on corncob particles are within the following ranges:

Example #7

Using surfactants as adherent coating: anionic, cationic and amphoteric can be used. The formulation is: foam obtained from adding water to about 0.02% to about 5% of surfactant by weight. The quantity of foam on a per weight basis to corncob woody ring fraction (carrier) is between about 0.5% and about 3.5%. Larger proportions do not allow for an appropriate mixture when adding active ingredients in solid form.

Example #8

Using mineral oils as an adherent coating; they should be highly refined preferably odor and colorless; viscosity on the Saybolt scale (SUS/210 F) should be between about 40 and about 300. The concentration of mineral oil by weight to woody ring is between about 0.5% and about 18%.

Finally, active ingredients can be polymers, perfumes, oxidizers, attractants, repellents, reducers, antibacterials, etc. in solid form. These ingredients are mixed and dispersed with the granular corncob carrier sized between about 37 and about 250 microns. The quantity of solid active ingredient dispersed should be between about 1% and about 40% per weight basis.

The examples described above can be characterized by the following:
1. A carrier formed by particles obtained from one of the woody ring and chaff portion of the corncob;
2. The particles having less than about 1% of fines by weight;
3. The particles having a moisture content below about 13%;
4. An active ingredient mixed with the carrier consisting of polymers, fragrances, perfumes, flavors, oxidizers, attractants, repellents, reducers and antibacterials, in either a liquid or solid state; and
5. An adherent comprising a surfactant, mineral oil and an organic oil.

Although these examples worked well for adsorbing undesirable odors from the air, it is desirable to provide a carrier that is capable of adsorbing malodors from all three states of matter: 1) gas; 2) liquid and 3) solid. In addition, it would be desirable to provide a carrier comprising a semi-rigid colloidal dispersion of a solid with a liquid or gas, such as a gel, jelly, glue, and the like, that is capable of adsorbing undesirable odors.

It has been discovered that aside from the woody ring and chaff portions of the corncob, other portions of the corncob also adsorb odoriferous substances, namely bees wing and pith portions. In addition, other compositions of matter, such as saw dust, granules or particles from any type of wood, powder, shavings, granules or particles from bamboo powder or flour, milled straw, cellulose, hemicelluloses and lignin adsorbent minerals, silica, zeolite and polysaccharides such as dextrose and starch either individually or mixed, are characterized by its qualities to adsorb scents present in gas, liquid and solid states of matter, while simultaneously serving as a carrier for any active ingredient or combination of active ingredients. Active ingredients are gradually released by the carrier or combination of carriers.

Some examples for the formulation of the adsorbent carrier with active substances in a gas state are:

Example #1

Different Corn Cob Fractions Adsorbency/Odor Reduction Performance
  Analytical Method using Colorimetric Gas Detection Tubes
  Target compound: Methyl Mercaptan and Isoamyl Amine
  Differences in malodor adsorption between different fractions/mixes were observed
  Mixes of fractions are equal parts in a per weight basis.

| | CC Fraction | | | | | | |
|---|---|---|---|---|---|---|---|
| | Pith + Bees Wing | Bees Wing | Bees Wing + Chaff | Chaff | Pith + Bees Wing + Chaff + Wood Ring | Woody Ring + Chaff | Woody Ring |
| (ppm) | 0.50 | 0.50 | 0.60 | 0.6 | 1 | 1 | 1.45 |
| Reference (ppm) | 9.0 | 7.9 | 8 | 8 | 8.25 | 7.8 | 9.8 |
| Malodor Reduction (percent) | 94.44 | 93.67 | 92.5 | 92.5 | 87.88 | 87.18 | 85.2 |

Mix of corn cob fractions can be milled or ground to obtain different particle sizing-from finest powders to the largest granules obtainable as known in the art-from individual corncob fractions, all of which comprise a mix of celluloses, hemicelluloses and lignin. Particle sizing depends on the desired contact surface area which in turn depends on the application and targeted odors and active ingredients. Particle sizing is measured in the art using U.S. Standard mesh screens sieves.

Particle sizing range for corncob or other described materials pass mesh U.S. Std mesh #3½ (about 5664 microns) and retained on U.S. Std. mesh #635 (about 20 microns).

Corncob fraction, cellulose, hemicellulose or mix and composition of matter can be in powder form or any agglomerate known in the art, such as but not limited to; pellets, reground or coarsely broken pellets, compressed tablets, pads etc. Additionally, powder or compressed form (s) may be encapsulated or put in a pouch or other containers.

All corncob fractions comprise cellulose, hemicelluloses and lignin. It has been observed that other sources of cellulose, hemicelluloses and lignin, such as but not limited to: saw dust from wood, bamboo powder or flour etc. provide adsorbency of odoriferous substances and can be used individually or mixed with of corn cob fractions.

Result: It has been determined that lignin from maize/ Lignin
Peroxides/Lignin Alkali or Lignin obtained by any other process, when added to corncob fractions and/or different mixes of cellulose, hemicelluloses and lignin containing material, significantly enhances odor adsorbency.

Example 2

Corn Cob Fraction is Woody Ring/Bamboo Lignin Blend, Malodor Reduction
  Analytical Method using Colorimetric Gas Detection Tubes
  Lignin sourced from Sigma Aldrich.
  Target compound: Pyridine
  Synergy between Woody Ring (WR)/Hard Woody Ring (HWR) Fraction and Lignin was observed

| | WR + 60% Lignin | WR + 20% Lignin | WR |
|---|---|---|---|
| Malodor Reduction (percent) | 98.9 | 89.1 | 82.5 |

It has been determined that corncob fractions comprise cellulose, hemicelluloses and lignin. It has been observed that other sources of cellulose, hemicelluloses and lignin, such as but not limited to: saw dust from wood, bamboo powder or flour etc. have adsorbency of odoriferous substances and are well suited to adsorb odoriferous substances such as ammonia, trimethylamine, skatole, isovaleric acid, 3 methyl-2-hexinoic acid, 3-mercapto-3-methyl hexanol, dimethyl disulfide, p-Cresol commonly found emanating from human and animal bodily fluids such as feces, urine, sweat and other human or animal bodily malodors. Animal bodily waste malodors such as but not limited to dog and cat feces and urine. Adsorbency of these malodors also apply to present invention, making this composition of matter, suitable but not limited to use in baby diapers, adult diapers, feminine protection pads, portable toilets, latrines cat litters and other applications where human or animal bodily odoriferous substances are present.

Based on the results from the above two Examples, a new composition of matter for use in controlling bodily malodors has been developed and tested with portable toilets, latrines, feminine protection pads, adult diapers and baby diapers. The new composition of matter consists of:

- Individual corncob fractions or mix of corncob fractions and/or other cellulose, hemicellulose and lignin source.
- Liquid fragrance or fragrance encapsulated or mixed with materials, such as but not limited to, silica, specialty silicas, synthetic amorphous silica, dextrose, zeolite, silica/aluminum oxide, and the like.
- Coating of encapsulated fragrance or any active ingredient, with materials such as but not limited to mineral oil, vegetable oil, animal oils, polymers and any other coating material, known in the art to coat and control the release of encapsulated fragrance or active ingredients.
- Other additives may be utilized, depending on objectives sought, such as PH buffering, surfactants and dispersants, hence light acids, solvents, such as dipropylene glycol, isopropyl myristate and benzyl benzoate or a light mineral oil may be added.

The new composition of matter can be in powder form or any form of compressed powder or agglomerate known in the art, such as, but not limited to; pellets, tablets, pads etc. Additionally, powder or compressed forms may be encapsulated or put in a pouch.

Some examples for the formulation of the adsorbent carrier with active substances in a liquid state are:

Example #1

Human Malodor Preparation:

Collect fresh human fecal and human urine from 4 donors place fecal and urine materials in separate containers and mix. Weigh each material and adjust individual weight to obtain 30% w/w fecal material and 70% w/w urine. Mix until a homogeneous mixture is obtained. Weigh mix. Divide mix evenly by weight in 4 glass bottles. Bottle one is control/reference, bottle two is added and mixed with 1 g of composition of matter object of this invention, bottle three is added and mixed with 1 g of deodorant fragrance, bottle four is added and mixed 1 g deodorant fragrance previously admixed with zeolite sized to pass 100 U.S. Std Mesh. Place in a laboratory oven such as a Heratherm General Protocol Oven set to 37 C and let stabilize for 24 hrs. Take bottles out of oven and have previously calibrated panelists evaluate bottles randomly.

RESULTS: Using a Labeled Magnitude Scale "LMS" (Green BG, Dalton P, Cowart B, Shaffer G, Rankin K and Higgins J 1996. Evaluating the "Labeled Magnitude Scale" for measuring sensations of taste and smell. Chemical Senses. 21(3):323-334.)

| | Bottle | | | |
| --- | --- | --- | --- | --- |
| | 1 | 2 | 3 | 4 |
| Contents | Reference Fecal Urine Mix | Fecal Urine Mix + 1 g Composition of Matter added | Fecal Urine Mix + 1 g Dedoorant fragrance added | Fecal Urine Mix + 1 g Dedoorant fragrance + zeolite added |
| Panelist Average Mal Odor Evaluation | Strongest imaginable | Barely Detectable | Very Strong | Very Strong |

Some examples for the formulation of the adsorbent carrier with active substances in a solid state are:

Example #1

Malodor Control in a Solid Soap Materials
  Soap Base (Fish Oil Base Laundry Bar from Asia)
  Standard Laundry Bar Fragrance
  Composition of matter/system
  Scale
  Screw Extruder
  Press with a bar soap shape mold.
  Closed container
  Sample and at least one Test sample are required.
  1. Determine Fragrance Proportion/Dose

| For Example: | Laundry Soap Base | 99.70% |
| --- | --- | --- |
| | Fragrance | 0.30% |

2. Weigh soap base and required fragrance.
3. Extrude soap base one time in a Screw Extruder.
4. Put extruded soap base in a container.
5. Add fragrance to the soap base and mix
6. Extrude the soap base plus fragrance mixture two more times.
7. Compact mixture in a press to form soap bars.
8. More maceration purposes put soap bars in a closed container for 72 hours before soap bar in use/wash test and/or sensory evaluation Results

| | Soap | | | |
| --- | --- | --- | --- | --- |
| | 1 | 2 | 3 | 4 |
| Contents | Reference Laundry Soap Base Only No Fragrance | Laundry Soap Base 99.70% + Fragrance 0.30% | Laundry Soap Base 99.70% + Fragrance 0.40% | Laundry Soap Base 99.70% + Fragrance 0.40% + Composition of Matter/System |
| Panelist Average LMS Scale Mal Odor Evaluation | Strong | Moderate | Moderate | Barely Detectable |

In conclusion, the incorporation of corncob fractions mentioned with active ingredients, whether chemically synthesized or natural, improves the qualities and functionality that both elements have for themselves separately. Further, the use of corncob particles from all four parts of the corncob as an adsorbent of odoriferous substances from the environment is also a novel concept. In addition, the carrier can be made from other celluloses and/or their basic chemical composition, cellulose, hemicelloloses, lignin, adsorbent minerals, such as, but not limited to, silica and zeolite, polysaccharides, such as dextrose and starch, either individually or mixed. Examples of the above, but not limited to, are: saw dust, granules or particles from any type of wood, powder, shavings, granules or particles from bamboo powder or flour, milled straw, cellulose, hemicelluloses and lignin adsorbent minerals, silica, zeolite and polysaccharides such as dextrose and starch either individually or mixed. The forms of carrying out the mixture or integration of these elements can vary according to the circumstance. The types of active ingredients that will be used depend on the functional objective that is pursued, equipment available and the experience of those skilled in the art.

The patents and publications referred to herein are hereby incorporated by reference.

Having described presently preferred embodiments the invention may be otherwise embodied within the scope of the appended claims.

What is claimed is:

1. A composition of matter for adsorbing scents and releasing active ingredients, comprising:
    a carrier having particles obtained from a corncob fraction comprising cellulose, hemicelluloses and lignin;
    an additive comprising a lignin additive, wherein the lignin additive comprises one of a lignin peroxide, a lignin alkali, and any combination thereof; and
    an active ingredient mixed with the carrier.

2. The composition of claim 1, wherein one of saw dust and bamboo powder are added to the corncob fraction.

3. The composition of claim 1, wherein the active ingredient comprises polymers, fragrances, perfumes, flavors, oxidizers, pesticides, fertilizers, attractants, repellents, reducers, hormones, enzymes, an anti-bacterial, and biocides, in a gas, liquid or a solid state, or a combination thereof.

4. The composition of claim 1, wherein the active ingredient ranges between 0.01% and 50.0% by weight.

5. The composition of claim 1, wherein the carrier is impregnated with an adherent substance.

6. The composition of claim 5, wherein the adherent substance is a solution of surfactant foam formed by adding 0.02% to 5% by weight of surfactant to water.

7. The composition of claim 5, wherein the adherent substance is one of a mineral oil and an organic oil with a viscosity on a Saybolt scale (SUS/210 F) of between 40 and 300.

8. The composition of claim 1, wherein the particles of the carrier further comprise one of silica, a specialty silica, a synthetic amorphous silica, dextrose, a starch, zeolite, silica/aluminum oxide, or any combination thereof.

9. The composition of claim 1, wherein the corncob fraction further comprises one of a bees wing, a woody ring, a chaff ring and a pith of a corncob.

* * * * *